United States Patent
Calkins

(10) Patent No.: US 9,248,314 B2
(45) Date of Patent: Feb. 2, 2016

(54) PERFORATED NONSLIP NON-ADHESIVE SURFACE COVERING

(75) Inventor: Mark A. Calkins, La Mirada, CA (US)

(73) Assignee: KITTRICH CORPORATION, Pomona, CA (US)

(*) Notice: Subject to any disclaimer, the term of this patent is extended or adjusted under 35 U.S.C. 154(b) by 0 days.

(21) Appl. No.: 13/426,271

(22) Filed: Mar. 21, 2012

(65) Prior Publication Data

US 2012/0183715 A1 Jul. 19, 2012

Related U.S. Application Data

(63) Continuation-in-part of application No. 13/022,468, filed on Feb. 7, 2011, now Pat. No. 9,132,283.

(60) Provisional application No. 61/432,906, filed on Jan. 14, 2011.

(51) Int. Cl.
| | |
|---|---|
| *B32B 3/24* | (2006.01) |
| *A61N 5/10* | (2006.01) |
| *A61B 6/03* | (2006.01) |
| *A61B 6/04* | (2006.01) |
| *A61B 6/00* | (2006.01) |
| *B32B 3/26* | (2006.01) |
| *B32B 3/30* | (2006.01) |
| *B32B 5/18* | (2006.01) |
| *B32B 7/12* | (2006.01) |
| *B32B 7/14* | (2006.01) |
| *B32B 27/12* | (2006.01) |

(52) U.S. Cl.
CPC ............. *A61N 5/1039* (2013.01); *A61B 6/032* (2013.01); *A61B 6/0457* (2013.01); *A61B 6/405* (2013.01); *A61B 6/4085* (2013.01); *A61B 6/481* (2013.01); *A61B 6/482* (2013.01); *A61B 6/507* (2013.01); *A61B 6/541* (2013.01); *B32B 3/266* (2013.01); *B32B 3/30* (2013.01); *B32B 5/18* (2013.01); *B32B 7/12* (2013.01); *B32B 7/14* (2013.01); *B32B 27/12* (2013.01); *A61N 5/103* (2013.01); *B32B 2262/02* (2013.01); *Y10T 156/1041* (2015.01); *Y10T 156/1057* (2015.01); *Y10T 428/15* (2015.01); *Y10T 428/24322* (2015.01); *Y10T 428/24496* (2015.01); *Y10T 428/24504* (2015.01); *Y10T 428/24851* (2015.01); *Y10T 428/24995* (2015.04); *Y10T 428/249953* (2015.04); *Y10T 428/249982* (2015.04); *Y10T 428/249985* (2015.04); *Y10T 428/249987* (2015.04); *Y10T 428/249991* (2015.04); *Y10T 428/249992* (2015.04); *Y10T 428/249993* (2015.04)

(58) Field of Classification Search
CPC .............................. Y10T 428/15; B32B 2/266
USPC ............................................... 428/43, 90, 141
See application file for complete search history.

(56) References Cited

U.S. PATENT DOCUMENTS

| | | |
|---|---|---|
| 3,143,208 A | 8/1964 | Sizemore |
| 3,706,636 A | 12/1972 | Bride |
| 5,198,275 A | 3/1993 | Klein |

(Continued)

*Primary Examiner* — Alexander Thomas
(74) *Attorney, Agent, or Firm* — Leason Ellis LLP

(57) ABSTRACT

The present disclosure relates to removable, nonslip, non-adhesive coverings which are used as shelf, drawer or storage liners. In particular, the covering sheet features an improved composite material having a top decorative layer of flocked polymeric film combined to a continuous bottom layer of unsupported foam. The structure of the multilayered composite material facilitates the convenient hand tearing of the sheet to size through a grid of perforations that are obscured by a fine coating of natural or synthetic fibers.

21 Claims, 3 Drawing Sheets

(56) References Cited

U.S. PATENT DOCUMENTS

| | | | |
|---|---|---|---|
| 5,217,781 A * | 6/1993 | Kuipers | 428/85 |
| 5,854,144 A * | 12/1998 | Hawley | 442/56 |
| 6,007,886 A | 12/1999 | Takigami | |
| 6,238,762 B1 | 5/2001 | Friedland et al. | |
| 2002/0182102 A1 * | 12/2002 | Fontenot et al. | 422/5 |
| 2003/0152761 A1 * | 8/2003 | McCune | 428/319.3 |
| 2009/0004433 A1 * | 1/2009 | Privitera et al. | 428/143 |

* cited by examiner

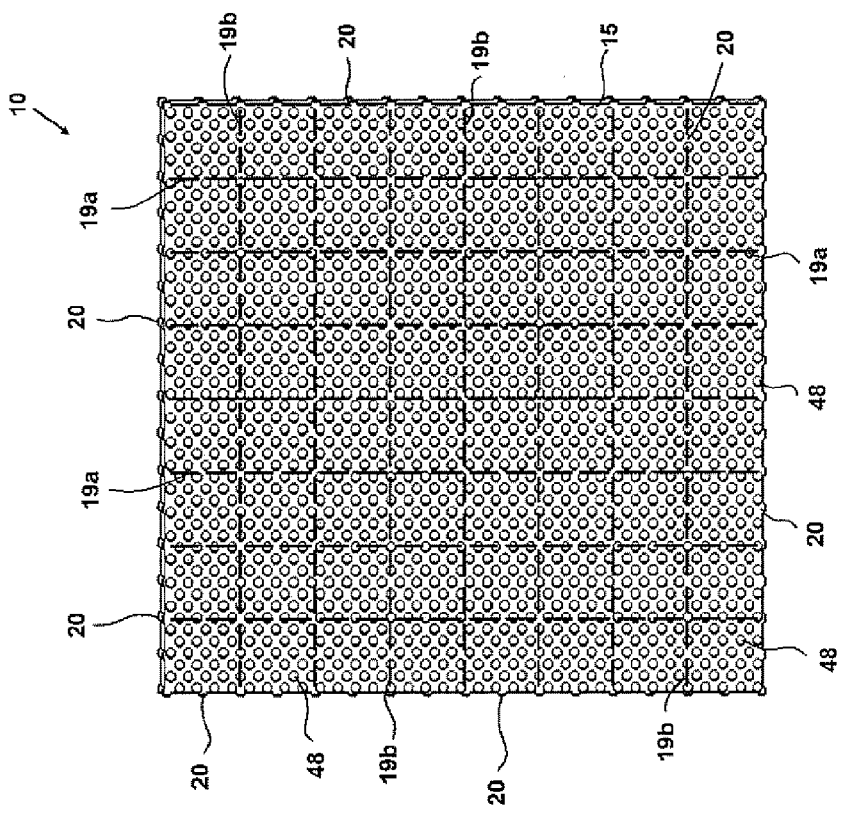
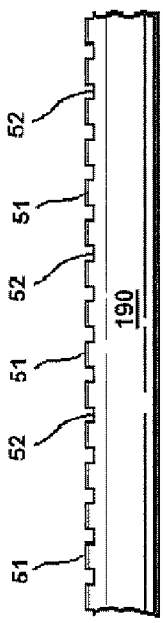

PERFORATED NONSLIP NON-ADHESIVE SURFACE COVERING

This application is a Continuation-In-Part Patent Application claiming the benefit of priority under 35 U.S.C. 120 from U.S. patent application Ser. No. 13/022,468 filed Feb. 7, 2011 now U.S. Pat. No. 9,132,283, which claims the benefit of priority from U.S. Provisional Patent Application No. 61/432,906 filed Jan. 14, 2011, the entire contents of which are herein incorporated by reference.

BACKGROUND OF THE INVENTION

1. Field of the Invention

The present invention is directed to removable, nonslip, non-adhesive coverings which are used as shelf, drawer or storage liners. In particular, the covering sheet features an improved composite material having a top decorative layer of flocked polymeric film combined to a continuous bottom layer of unsupported foam. The structure of the multilayered composite material facilitates the convenient hand tearing of the sheet to size through a grid of perforations that are obscured by a fine coating of natural or synthetic fibers.

2. Description of the Prior Art

Shelf, drawer or storage liners have been extensively sold at retail venues and are available in a selection of self-adhesive or non-adhesive coverings. Printed wall coverings or papers were once used to protect the wooden interiors of cabinets or drawers from exposure to moisture. These permeable materials were eventually replaced with the application of decorative self-adhesive plastic sheets, which provide a greater degree of water resistance to the unfinished or varnished surfaces of cupboards. Self-adhesive shelf liners primarily consist of a facing layer of transparent, opaque or printed polymeric film coated with an underlying layer of pressure sensitive adhesive. The pressure sensitive adhesive may be combined with a siliconized release liner, which is removed prior to the application of the decorative plastic laminate. To assist the consumer in the installation of the product, the release liner typically features an imprinted grid of guide lines following the vertical and horizontal axes of the covering. The interior dimensions of cabinets or drawers are then transferred to the printed release liner prior to cutting the shelf liner to size.

Similarly, another provision known in the art includes a multilayered surface covering featuring a decorative fabric laminated to an intermediate carrier sheet having a base layer of adhesive. The shelf liner is typically available with a fabric facing composed of non-woven synthetic filaments or, alternatively, a woven textile. A paper release liner, comprising the same arrangement of imprinted guide lines commonly found on self-adhesive plastic coverings, envelops the layer of adhesive until final application of the decorative laminate.

In the prior art, the application of self-adhesive coverings is known to become frequently unmanageable. It is difficult to accurately achieve consistent straight cuts along the length and width of the material, even with the added convenience of an imprinted release liner, and especially when the shelf liner is a multilayered composition. Irregular, oversized or non-conforming laminates that will not precisely adhere to their intended surfaces may result in the formation of entrapped air pockets beneath these impermeable coverings. Such air pockets eventually collapse under load, permanently causing unsightly creases and wrinkles. Moreover, a further problem emerges when the exposed adherent layer inadvertently folds upon itself, as the separation of these mutually bonded surfaces results in the irreparable deformation of the shelf liner.

Previous attempts have been made in the prior art to simplify the alteration of self-adhesive shelf liners so that they may correspond to the dimensions of cabinets and drawers. For example, earlier methods include the provision of forming lines of weakness into a laminate sheet to facilitate the hand-tearing of the covering to fit a surface of predetermined size.

U.S. Pat. No. 6,238,762, issued on May 29, 2001 to R. Friedland et al., discloses a self-adhesive decorative covering adapted with through-cut microperforations and embossed prescores, which are oriented at right angles, to provide rectilinear yield lines enabling the manual hand sizing of a sheet. Lines of weakness may also run diagonally between the grid of microperforations to facilitate changes in the direction of tearing. The disclosure further includes a provision for extending the embossed prescores partially through the profile of the laminate. The arrangement of through-cut microperforations and embossed prescores may be used in combination with a self-adhesive covering having a separable release liner that includes a corresponding pattern of perforations or, alternatively, with a self wound sheet having a releasable polysiloxane facing.

U.S. Pat. Nos. 4,380,564 and 4,465,729, issued on Apr. 19, 1983 and Aug. 14, 1984, respectively, to Cancio et al., disclose a plastic laminate having an intersecting grid of tear lines formed into the surface of the sheet material whereby the film may be torn by hand in more than one direction. In a preferred embodiment presented in both patents, the plastic sheet materials are composed of a polymeric component consisting of a low density polyethylene having a disperse phase of calcium carbonate, with the preferred ratio of the foregoing ingredients contingent upon the dimension of the grid pattern embossed into the film. The inventors claim that the selected admixtures of polyethylene and calcium carbonate enhance the tear assisting provision of their polymeric sheet while maintaining the overall tensile strength characteristics of the material. In each disclosure, a layer of adhesive may be disposed on one side of the plastic covering, which is protected by a release liner that does not have any cross-tearable lines. Accordingly, installation of the materials taught in both patents first requires the removal of the release liner prior to hand tearing the laminate to size.

The primary disadvantage of the prior art, inherent within self-adhesive coverings which integrate perforated or cross-tearable features, concerns the inadvertent separation of the shelf liner along unselected lines of weakness, especially when attempting to pull apart mutually adhering surface portions that have accidentally folded upon themselves. The strong reciprocal bond created through such mishaps may surpass the tensile strength property of the yield lines, causing the unintended fragmentation of the plastic sheet, thereby rendering the covering unsuitable for installation. Moreover, another difficulty relates to the replacement of perforated or cross-tearable laminates after long-term use, as the molecular structure of the polymeric film degrades with age, while the self-adhesive coating becomes fully cured to the interior surfaces of cabinets or drawers. Consequently, the increased bond strength of the adhesive, combined with the embrittlement of the plastic, will result in the adverse disintegration of the material into miniscule pieces upon removal.

Although the use of self-adhesive coverings in the prior art have long provided consumers with the means to both decorate and protect shelving and drawers, the thin layer of polymeric film often fails to conceal uneven surface flaws or irregularities. More recently, the renovation or construction of kitchens and bathrooms now feature cabinets with water-resistant interior laminates, sold commercially under the Wilsonart® or Formica® brands, which are primarily manufactured from thermosetting plastic resins. Since the latest cabinet fabrications also use composite particle board materials, the application of such laminates inhibits moisture from coming into contact with the bonded wooden fibers and produces a smooth consistent surface that can be easily cleaned. Where functionality and durability is therefore enhanced, the thermoset resin permanently hardens under heat and pressure during the formation of these laminates, thereby increasing the rigidity while diminishing the impact resistance of the material. Without the benefit of a suitable protective covering, the striking force of ordinary household articles can cause pieces of the thermoset plastic sheet to break away from shelving or drawers. In view of the fact that self-adhesive coverings offer superficial protection against impact resistance, and their subsequent removal often leaves behind a viscous residue, non-adhesive shelf liners have gained widespread acceptance.

One type of non-adhesive shelf liner in the prior art consists of a knitted polyester scrim with a coating of thermally foamed polyvinyl chloride (PVC) resin. The knitted construction of the scrim provides an arrangement of woven yarns defining a pattern of apertures that correspond to a configuration of openings extending through the thickness of the cured PVC material. Alternatively, the PVC resin may be knife coated to both sides of a knitted scrim devoid of openings, or to a non-woven fabric of autogenously bonded polyester fibers, producing a solid continuous layer of supported foam. The PVC compound also includes a plasticizer that imparts a removable nonslip mechanical bond between the shelf liner and an applied surface. Such coverings provide a degree of protective cushioning and are often laminated or fused with a top decorative layer of plastic film. The basic deficiency of foamed non-adhesive liners is that they do not incorporate any provision for the consumer to conveniently alter the product to match the interior dimensions of cabinets or drawers. Moreover, the overall thickness of the shelf liner, along with the variable density of the knitted scrim and thermally cured foam, makes it difficult to maintain the uniform alignment of cuts along the length and width of the material.

Further, prior art methods—which are used to configure cross-tearable features within self-adhesive shelf liners—cannot be successfully applied to form lines of weakness in removable, nonslip, non-adhesive versions that are supported with a knitted scrim or non-woven fabric. The embossment of an intersecting grid of tear lines will not adequately diminish the tensile strength property of the woven yarns or bonded polyester fibers, where the perforation of a linear series of discontinuous holes will not effectively weaken adjacent segments of imperforated substrate. The adaptation of these coverings for hand tearing becomes even less viable with the added combination of a laminated layer of decorative fabric.

U.S. Pat. No. 5,707,903, issued on Jan. 13, 1998 to H. Schottenfeld, discloses a nonslip laminated liner comprising a foamed PVC coated scrim with a vinyl sheet covering. The scrim increases the tensile strength properties of the foamed nonslip pad, which includes a plurality of open cells extending through the thickness of the cured PVC material. Additionally, the vinyl sheet covering is permanently bonded to the top plane of the nonslip pad.

U.S. Pat. No. 5,854,144, issued on Dec. 29, 1998 to J. Hawley, describes a nonslip multilayer sheet material for covering household surfaces. The cushioned shelf liner is made by laminating a layer of thin plastic film to the top surface of a spunbonded non-woven polyester fabric. The bottom surface of the non-woven fabric is coated with a continuous layer of polyurethane foam.

U.S. Pat. Nos. 5,863,845 and 5,874,371, which respectively issued on Jan. 26, 1999 and Feb. 23, 1999 to T. Owen, similarly disclose a removable non-skid, non-adhesive surface covering comprising a woven substrate having a plurality of apertures, wherein at least a portion of the bottom surface of the substrate is coated with a PVC resin. Alternatively, a non-woven substrate may also be used. The application of the polymeric compound prevents the covering from skidding tangentially or laterally in a plane parallel to an applied surface. A decorative sheet is adhered to the top surface of the non-skid covering.

U.S. Pat. No. 6,022,617, issued on Feb. 8, 2000 to M. Calkins, discloses a laminated nonslip liner or mat having an intermediate layer of non-woven material printed on one side with a pattern of relatively high friction material. The imprinted pattern consists of a high density matrix of latex or PVC projections. A decorative vinyl sheet is laminated to the obverse side of the non-woven material. Similarly, U.S. Pat. No. 6,159,583, issued on Dec. 12, 2000 to the same inventor, discloses a laminated non-slip liner or mat comprising an interposing layer of non-woven material printed with a high density matrix of polyethylene projections. The imprinted thermoplastic resin provides non-adhering, non-marring contact with an underlying surface.

U.S. Pat. No. 6,221,796, issued on Apr. 24, 2001 to J. Hawley et al., describes a laminated shelf lining material having nonslip characteristics. The covering is produced by bonding a smooth continuous layer of vinyl film to a layer of scrim comprising woven threads surrounded by a foamed PVC plastic. Comparatively, U.S. Pat. No. 6,130,174, issued on Oct. 10, 2000 to the same inventor, discloses a smooth surfaced foam laminate and a method for making the material similar to the Hawley '796 patent.

U.S. Pat. No. 7,253,126, issued on Aug. 7, 2007 to W. Browne, discloses a decorative nonslip shelf liner that comprises a multi-layered thermoplastic composite sheet. A decorative top layer of a thin polyvinyl chloride film is laminated or fused to a non-slip bottom layer via a disposed interlayer of polyvinyl chloride plastisol. The non-slip bottom layer consists of a supporting non-woven fabric coated on both sides with a foamed plasticized polyvinyl chloride resin.

U.S. Patent Application Publication US 2003/0036323 A1 by R. Aliabadi, published on Feb. 20, 2003, discloses a multilayered nonslip plastic shelf liner comprising an intermediate layer of fibrous polyester fabric enveloped by two thermally bonded layers of polyvinyl chloride. A thin coating of polyurethane is applied to the obverse side of the covering to provide a smooth frictionless surface, where the reverse side remains uncoated to impart nonslip properties to the laminated material.

None of the above inventions and patents, taken either individually or in combination, is seen to have solved the aforementioned problems associated with resizing a removable, nonslip, non-adhesive, multilayered surface covering having a decorative fabric facing.

Accordingly, it is an object of the present invention to provide an improved removable, nonslip, non-adhesive surface covering having a facing layer of natural or synthetic fibers, which are bonded to a composite material featuring a grid of perforations that facilitate the convenient hand tearing of the shelf, drawer or storage liner to size.

It is an additional object of the invention to provide a removable, nonslip, non-adhesive surface covering having an intermediate reinforcing layer of polymeric film combined to a continuous bottom layer of unsupported calendered foam.

Finally, an object of the invention is to provide a removable, nonslip, non-adhesive surface covering having an underlying layer of unsupported calendered foam configured with a fine pattern of micro-embossed indentations to assist in the hand tearing of the material.

These and other objects of the invention will be apparent to those skilled in the art from the following detailed description of the preferred embodiments of the instant invention.

SUMMARY OF THE INVENTION

The disadvantages and limitations of the background art discussed above are overcome by the present invention. With this invention, a removable, nonslip, non-adhesive surface covering is provided, wherein an improved composite material having a top decorative layer of flocked polymeric film is combined to a continuous bottom layer of unsupported foam. The structure of the multilayered composite material facilitates the convenient hand tearing of the sheet to size through a grid of perforations that are obscured by a fine coating of natural or synthetic fibers.

In accordance with the present invention, the composite material includes a top-facing layer of finely cut natural or synthetic fibers which are bonded to a carrier sheet of polymeric film. The flock itself can be made out of various synthetic filaments, including acrylic, nylon, polyester, polypropylene and rayon. Alternatively, natural fibers such as cotton or wool may be used. The top facing surface of fibers may be cut into identical or random lengths and may be applied as a decorative textural pattern or, more preferably, in a continuous uniform layer. The fibers are affixed to the carrier sheet via a thin layer of wet adhesive; the coated polymeric film is then conveyed over a mechanical vibrating surface wherein an electrostatic charge orients the cut filaments to stand in a vertical position. The flocked surface is then dried and cured to bind the fibers to the polymeric carrier sheet. Through this means, the vertically extending projections of flock fiber conceal the grid of perforations that penetrate through the obverse layer of the shelf, drawer or storage liner.

In another aspect, the disclosed composite material incorporates an intermediate layer of polymeric film that reinforces the dimensional stability of the underling layer of unsupported foam. The polymeric film may be combined to the unsupported foam through the application of an interjoining layer of adhesive. In a specific embodiment, the intermediate layer may be a polyvinyl chloride sheet, although other synthetic films may be used. The polymeric sheet has sufficient tensile and tear strength properties along the machine and transverse directions of the film to inhibit failure of the multilayered composite material during perforation.

The underlying layer of unsupported foam consists of a polymeric compound having a diffusion of minuscule gas bubbles. In a preferred embodiment, the polymeric admixture is a polyvinyl chloride resin that includes a chemical foaming agent. The chemical foaming agent is selected from the group of hydrazine derivatives, and is more particularly an Azodicarbonamide powder that is suspended in the resin formulation. Under thermal decomposition, Azodicarbonamide releases nitrogen when exposed to temperatures in the range of 200° to 215° C., thereby causing the expansion of the polymeric composition. The polyvinyl chloride compound is cured by means of a thermal calendering process, wherein the polymeric admixture is uniformly coated on a releasable belt or casting paper which is compressed against a heated roller. In the absence of a knitted scrim or non-woven fabric substrate, the releasable belt or casting paper provides support and dimensional stability to the unsupported polymeric compound while maintaining the uniform thickness of the nonslip material during solidification. The heated roller, releasable belt or casting paper may be configured to impart a fine pattern of micro-embossed indentations on the bottom surface of the unsupported calendered foam. The micro-embossed indentations essentially weaken the tear strength properties of the nonslip layer and enhance the hand alteration of the perforated covering.

The present invention advantageously includes a grid of perforations that are oriented along the vertical and horizontal axes of the multilayered covering. The perforations extend through the profile of the composite material, and are produced with a rotary or flat bed die assembly having a series of perforating rules. The perforating rules consist of a sequence of projecting teeth which are separated at regular intervals by an arrangement of indented gaps. The sequence of projecting teeth incise a linear succession of perforations into the multilayered composite material, where the indented gaps form an alternating pattern of uncut tie portions which run adjacent to the incised perforations. The length of the projecting teeth or indented gaps may be of equivalent dimension along the vertical or horizontal axes of the surface covering or, alternatively, may be adapted to compensate for perpendicular variations in the tensile and tear strength properties inherent within the machine and transverse directions of the composite material.

Further objects and advantages of the present invention will be apparent from the following description of the preferred embodiments when considered in conjunction with the accompanying drawings.

BRIEF DESCRIPTION OF THE DRAWINGS

FIG. 2E is a cross-sectional view similar to FIG. 2A showing the multilayered construction of a fourth alternate embodiment of a removable, nonslip, non-adhesive surface covering according to the present invention;

FIG. 3 is a plan view showing micro-embossed indentations formed into the bottom unsupported foamed layer of a removable, nonslip, non-adhesive, multilayered surface covering according to the present invention; and FIG. 4 is a plan view of a perforating rule segment showing a sequence of projecting teeth and indented gaps for perforating a removable, nonslip, non-adhesive, multilayered surface covering according to the present invention.

Similar reference characters denote corresponding features consistently throughout the attached drawings.

DETAILED DESCRIPTION OF THE PREFERRED EMBODIMENTS

Figure 1:
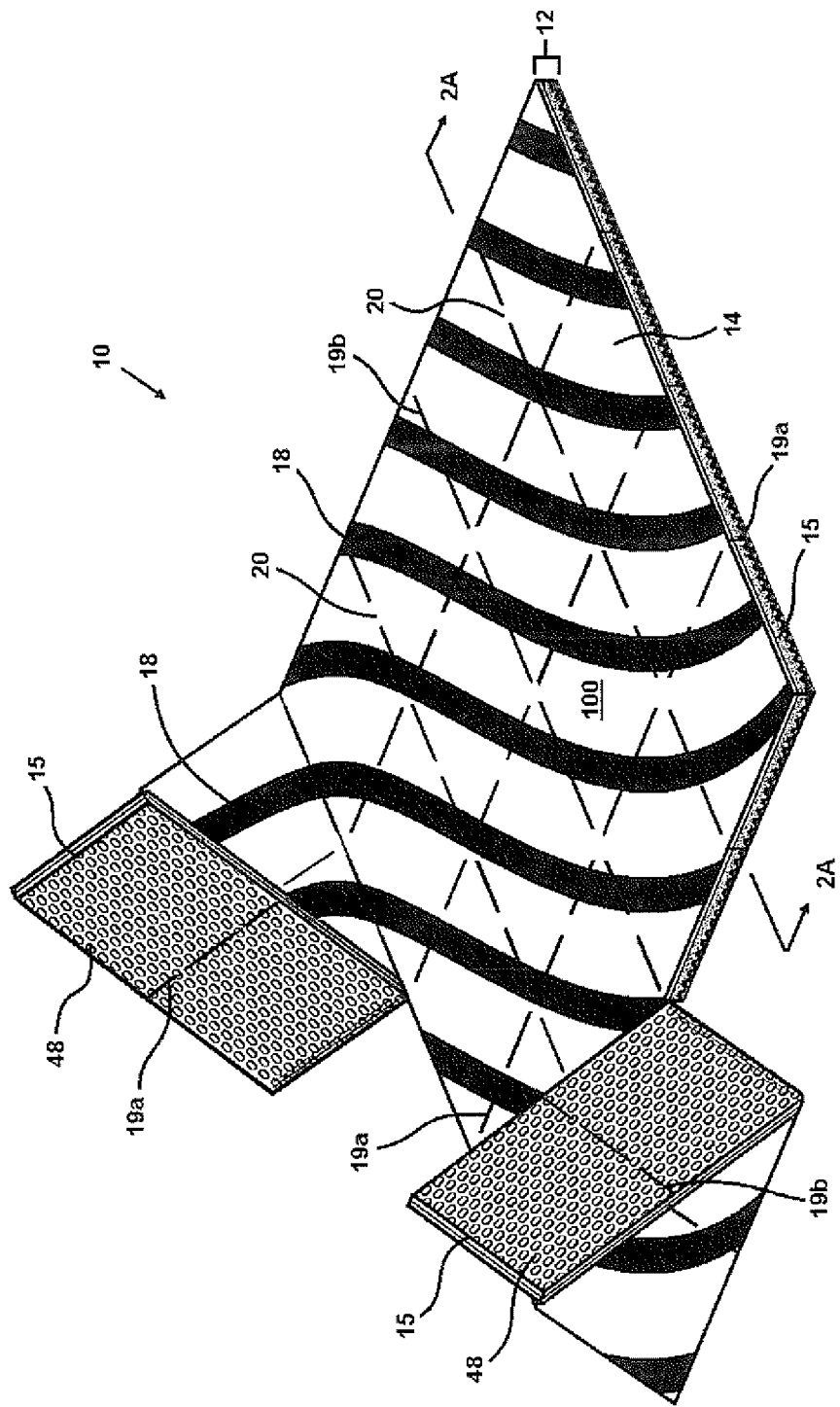
FIG. 1 is an enlarged perspective view of a removable, nonslip, non-adhesive surface covering according to the present invention, showing a perforated multilayered composite material with torn edge portions.

The present invention is a removable, nonslip, non-adhesive surface covering suitable for use as a shelf, drawer or storage liner, and designated generally as 10 in the drawings. With reference to FIG. 1 and FIGS. 2A-2E, the surface covering 10 is a multilayered composite material 12, having a top facing layer of flocked fibers 111, which are bonded to an intermediate carrier sheet of polymeric film 14. The intermediate carrier sheet 14 is combined to a continuous bottom layer of unsupported foam 15 through an interjoining layer of adhesive 17. The structure of the multilayered composite material 12 facilitates the convenient hand tearing of the shelf, drawer or storage liner through a grid of perforations 19a and 19b, which are obscured by the facing layer of bonded fibers 111.

Figure 2A:
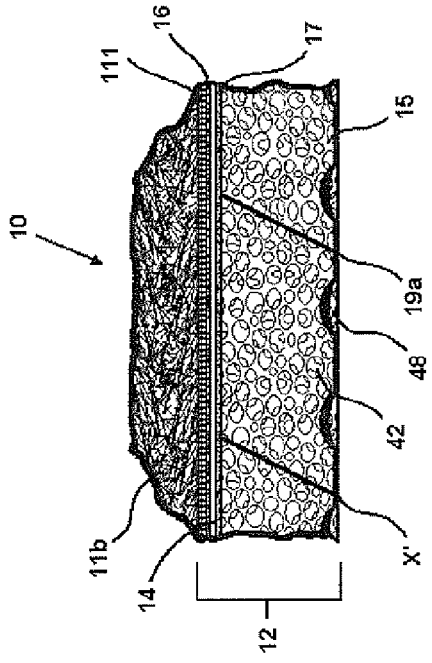
FIG. 2A is a cross-sectional view drawn from lines 2A-2A of FIG. 1, showing the multilayered construction of a removable, nonslip, non-adhesive surface covering according to the present invention.
Figure 2B:
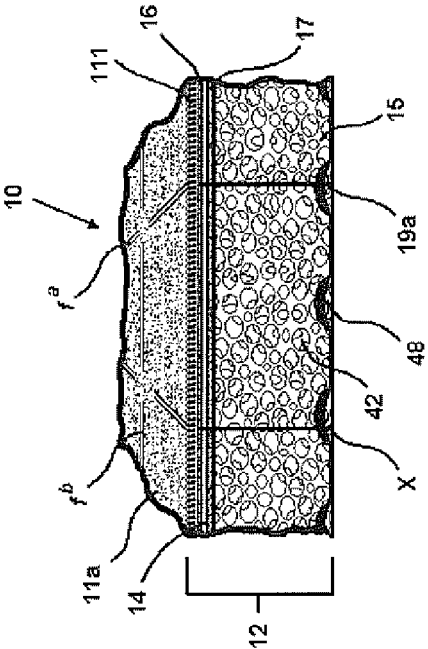
FIG. 2B is a cross-sectional view similar to FIG. 2A showing the multilayered construction of a first alternate embodiment of a removable, nonslip, non-adhesive surface covering according to the present invention.
Figure 2C:
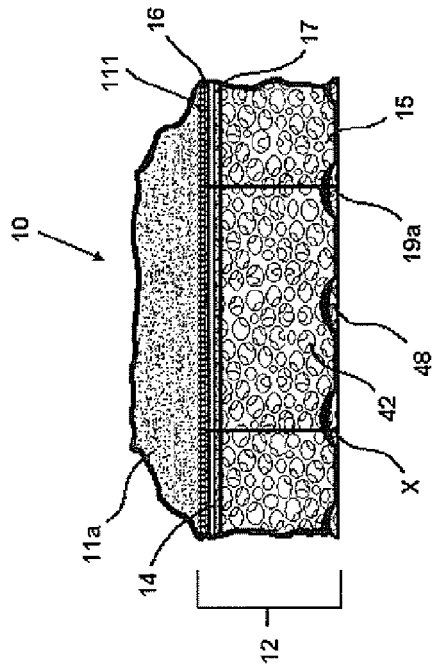
FIG. 2C is a cross-sectional view similar to FIG. 2A showing the multilayered construction of a second alternate embodiment of a removable, nonslip, non-adhesive surface covering according to the present invention.

The facing layer 11a, 11a, or 11c, as shown in FIGS. 2A-2C, is composed of finely cut natural or synthetic fibers 111, which are bonded to an intermediate carrier sheet 14 via a thin layer of adhesive 16. The fibers 111 may be of identical or random size, and are between 0.38 mm to 2.30 mm in length. In a preferred embodiment, the fibers 111 may be selected from the group of synthetic polymers including acrylic, nylon, polyester, polypropylene, and rayon, which have a denier weight in the range of 0.8 to 45 grams per 9000 linear meters of yarn. The bonded filaments 111 may be vertically oriented on the intermediate carrier sheet 14 to create a velour facing layer $11^a$ or, alternatively, the fibers may be matted together through the application of heat and pressure to produce a felt facing layer $11^b$, or an artificial suede facing $11^c$. In view of the fact that the synthetic filaments 111 will be subjected to a high degree of compressive force during the die cutting process, and to ensure optimal concealment of the resulting grid of perforations 19a and 19b, the polymeric fibers should be resistant to stress-whitening.

Figure 2D:
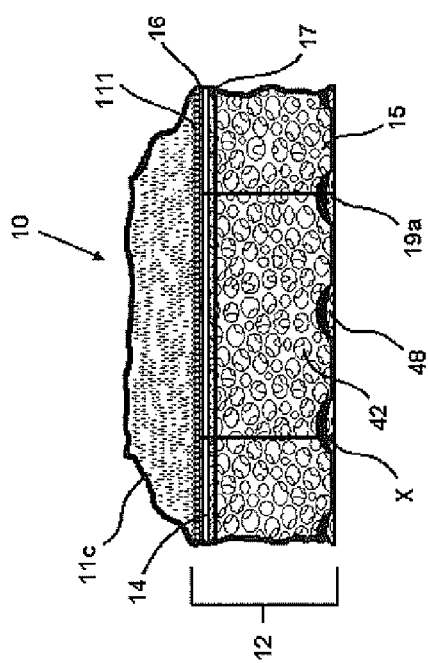
FIG. 2D is a cross-sectional view similar to FIG. 2A showing the multilayered construction of a third alternate embodiment of a removable, nonslip, non-adhesive surface covering according to the present invention.

In an alternate embodiment, and as shown in FIG. 2D, the tear-assisting provisions of the surface covering 10 may be perceptibly enhanced within the facing layer 11a through the application of synthetic filaments 111 that exhibit low impact resistance during perforation. The compressive force of the perforation process will cause effected filaments $f^a$ and $f^b$ to crease and subsequently lighten, thereby creating a faint grid within the facing layer 11a, which corresponds to the arrangement of perforations 19a and 19b incised into the surface covering 10. Fibers exhibiting such stress-whitening characteristics may be selected from the preferred group of acrylic or polypropylene filaments, although other synthetic fibers may be used.

Although the facing layer 11a, 11b, or 11c may consist of a continuous deposit of polymeric fibers 111, as illustrated in FIGS. 1 and 2E, the synthetic filaments can alternatively form a decorative motif 18 through the application of a corresponding pattern of adhesive 16'. In either embodiment, the layer of adhesive 16 or 16' may be selected from the group of plastisol or acrylic latex binding materials, which can be applied to the intermediate carrier sheet 14 through rotary screen printing or transfer roll coating, although other production methods may be used. The flocked surface 11a, 11b, 11c, or 18 is then dried and cured to bind the fibers 111 to the polymeric carrier sheet 14. The flocked facing layer 11a, 11b, or 11c can be subsequently enhanced with decorative patterns (not shown), which may be applied through the means of digital ink jet or rotary screen printing; ultrasonic pattern bonding can also be used to simulate the appearance of a quilted surface covering.

The intermediate layer of polymeric film 14 reinforces the dimensional stability of the underling layer of unsupported foam 15. The intermediate layer 14 may consist of single or multiple layers of thermoplastic film which can be extruded, calendered or cast from the group of polymers that include Polyvinyl Chloride (PVC); Polypropylene (PP); Polyethylene (PE); Polyester (PET); Ethylene Vinyl Acetate (EVA); or other appropriate polymeric formulations. Alternatively, the intermediate layer 14 may consist of a paper stock having a water resistant coating.

In a preferred embodiment, and as shown in FIGS. 2A-2D, the intermediate layer 14 is composed of a single layer of polyvinyl chloride film that is in the range of 0.075 mm to 0.1775 mm in thickness. The polyvinyl chloride sheet 14 has sufficient tensile and tear strength properties along the machine and transverse directions of the film to inhibit failure of the multilayered composite material 12 during perforation. The preferred tensile strength of the polyvinyl chloride layer 14, when measured according to the standard testing method for tensile properties of thin plastic sheeting under ASTM D-822, is in the range of 175-290 $kg/cm^2$ in the machine direction and 140-270 $kg/cm^2$ in the transverse direction of the polymeric film. Additionally, the tensile modulus of the plastic layer 14, when measured under the same ASTM protocol, is in the preferred range of 130-225 $kg/cm^2$ in the machine direction and 115-200 $kg/cm^2$ in the transverse direction of the film. The preferred tear resistance of the polyvinyl chloride layer 14, when measured according to the standard testing method for tear resistance (Graves Tear) of plastic film and sheeting under ASTM D-1004, is in the range of 50-90 kg/cm for both the machine and transverse directions of the polymeric sheet. The tensile and tear strength properties of the top facing layer 14 may be enhanced by increasing the thickness of the material or, alternatively, by using thermoplastic sheets that are composed of multiple layers of polymeric film 140 and 141, as illustrated in FIG. 2E.

As further shown in FIGS. 2A-2E, the intermediate layer of polymeric film 14 is combined to the unsupported foam 15 through the application of an interjoining layer of adhesive 17. The bonding agent 17 may be selected from the group of synthetic resins that includes Acrylic Polymers, Polyamides, Polyolefins, Polyurethanes, or other suitable adhesive systems. The layer of adhesive 17 may be solidified through the application of heat, ultraviolet light or electron beam curing methods. As an alternative, the adhesive layer 17 may be compounded to be a moisture curable formulation that may reactivate with the application of heat and pressure.

As detailed in FIGS. 2A-2E, and FIG. 3, the underlying layer of unsupported foam 15 consists of a polymeric compound having a diffusion of miniscule gas bubbles 42. The underlying layer of unsupported foam 15 may consist of natural or synthetic resins that include Latex; Polyvinyl Chloride (PVC); Polyurethane (PUR); Ethylene Vinyl Acetate (EVA); or other appropriate compounds. It can be appreciated that the polymeric compound may also contain additives that are standard in the art, including fillers, pigments, matting agents, UV inhibitors, flame-retardants, biocides, fungicides, and other ingredients. In a preferred embodiment, the polymeric compound is a polyvinyl chloride resin that includes a chemical foaming agent. The chemical foaming agent is selected from the group of hydrazine derivatives, and is more particularly an Azodicarbonamide powder that is suspended in the resin formulation. Under thermal decomposition, Azodicarbonamide releases nitrogen when exposed to temperatures in the range of 200° to 215° C., thereby causing the expansion of the polymeric composition.

In a preferred embodiment, the layer of unsupported polyvinyl chloride foam 15 is in the range of 1.275 mm to 1.675 mm in thickness, and configured with a fine pattern of micro-embossed indentations 48. The pattern of micro-embossed indentations 48 are alternately spaced at 0.889 mm intervals, although other micro-embossed configurations may also be used. The micro-embossed indentations 48 essentially weaken the tear strength properties of the unsupported foam 15 and enhance the hand alteration of the perforated surface covering 10. Alternatively, the uniform layer of cured polyvinyl chloride foam may be smooth on both sides.

With further reference to FIGS. 1, 2A-2E, and FIG. 3, the present invention includes a grid of perforations 19a and 19b that are oriented at right angles along the vertical and horizontal axes of the surface covering 10. The perforations 19a and 19b extend through the profile of the composite material 12, and penetrate the intermediate layer 14 of the shelf, drawer or storage liner 10. The perforations 19a or 19b may extend at perpendicular angles x through the profile of the composite material 12 or, as illustrated in FIG. 2B, the perforations 19a or 19b may extend through the composite material at beveled angles x'. In a preferred embodiment, to reduce the visible appearance of perforations scored into the surface of the shelf, drawer or storage liner 10, the perforations 19a and 19b are incised from the bottom of the unsupported foam layer 15 through the intermediate layer 14 of the composite material 12. Alternatively, the perforations 19a and 19b may be incised from the facing layer 11a, 11b or 11c through the unsupported foam layer 15. In a specific embodiment, the perforations 19a run linearly along the machine direction of the surface covering 10, and are spaced in parallel along the transverse direction of the material in 6.35 mm increments. Conversely, the perforations 19b run linearly along the transverse direction of the surface covering 10, and are spaced in parallel along the machine direction of the material in 6.35 mm increments. Accordingly, the corresponding series of perforations 19a and 19b produce a pattern of interconnecting square portions 100 having all four sides that are approximately 6.35 mm in length. In an alternate embodiment, the parallel arrangement of linear perforations 19a or 19b may not be equidistantly spaced along the machine or transverse directions of the surface covering 10. Moreover, the horizontal or perpendicular arrangement of linear perforations, 19a or 19b, may not be necessarily arranged at corresponding parallel intervals to form a uniform grid along the machine or transverse directions of the shelf, drawer or storage liner 10.

The perforations 19a and 19b are produced with a rotary or flat bed die assembly having a series of perforating rules that are oriented at right angles. As disclosed in FIG. 4, the perforating rules 190 consist of a sequence of projecting teeth 51, which are separated at regular intervals by an arrangement of indented gaps 52. The sequence of projecting teeth 51 incise a linear succession of perforations 19a and 19b into the composite material 12, where the indented gaps 52 form an alternating pattern of uncut tie portions 20 which run adjacent to the incised perforations. In a preferred embodiment, the projecting teeth 51 are each 2.38 mm in length, where the indented gaps 52 span a distance of 0.8128 mm each. In an alternate embodiment, the length of projecting teeth 51, or indented gaps 52, which are machined into the series of perforating rules 190, may be adapted to compensate for perpendicular variations in the tensile and tear strength properties inherent within the machine and transverse directions of the composite material 12. For example, if the tensile and tear strength properties of the composite material 12 are greater in the machine direction, than the tensile and tear strength properties oriented along the transverse direction, the perforating rules 190—which in this instance form the series of linear perforations 19a—would be altered to lengthen the dimension of each projecting tooth 51, while the span of each indented gap 52 would be similarly decreased. Accordingly, modification in the dimensioning of the projecting teeth or indented gaps equalizes the tear resistance of the perforated grid along the vertical and horizontal axes of the surface covering 10.

Even though numerous characteristics and advantages of the present invention have been set forth in the foregoing description, together with details of the structure and function of the preferred embodiments, the above disclosure is illustrative only. Changes may be made in detail, especially in matters of shape, size and arrangement of parts within the principles of the invention to the full extent indicated by the broad general meaning of the terms in which the appended claims are expressed.

What is claimed is:

1. A surface covering comprising:
a multilayered composite material, wherein the multilayered composite material further includes a plurality of vertical perforated lines and a plurality of horizontal perforated lines, the vertical and horizontal perforated lines forming a grid;
and further wherein,
the multilayered composite material further comprises (1) a top facing layer of synthetic fibers resistant to stress-whitening; (2) an intermediate layer of polymeric film wherein the polymeric film is comprised of single or multiple layers of thermoplastic film;
and (3) a continuous bottom layer of unsupported polyvinyl chloride foam.

2. The surface covering according to claim 1, wherein the top facing layer is composed of fibers that are in the range of 0.38 mm to 2.30 mm in length.

3. The surface covering according to claim 1, further comprising an adhesive layer in-between the top facing layer of fibers and the intermediate layer of polymeric film.

4. The surface covering according to claim 3, wherein the adhesive is selected from the group of plastisol or acrylic latex binding materials.

5. The surface covering according to claim 3, wherein the adhesive layer is continuously disposed on the intermediate layer of polymeric film.

6. The surface covering according to claim 3, wherein the adhesive layer is discontinuously disposed on the intermediate layer of polymeric film.

7. The surface covering according to claim 1, wherein the intermediate layer of polymeric film is selected from the group of polymers consisting of polyvinyl chloride, polypropylene, polyethylene, polyester, and ethylene vinyl acetate.

8. The surface covering according to claim 1, wherein the intermediate layer of polymeric film has a thickness in the range of 0.075 mm to 0.1775 mm.

9. The surface covering according to claim 1, further comprising an adhesive layer in-between the intermediately layer of polymeric film and the bottom layer of unsupported foam.

10. The surface covering according to claim 9, wherein the adhesive is selected from the group of bonding agents consisting of acrylic polymers, polyamides, polyolefins and polyurethanes.

11. The surface covering according to claim 1, wherein the bottom layer of unsupported polyvinyl chloride foam comprises a polymeric compound having a diffusion of gas bubbles.

12. The surface covering according to claim 11, wherein the bottom layer of unsupported polyvinyl chloride foam is configured with a fine pattern of micro-embossed indentations.

13. The surface covering according to claim 11, wherein the bottom layer of unsupported polyvinyl chloride foam has a smooth continuous surface.

14. The surface covering according to claim 1, wherein the bottom layer of unsupported polyvinyl chloride foam has a thickness in the range of 1.275 mm to 1.675 mm.

15. The surface covering according to claim 1, wherein the composite material is a shelf liner, a drawer liner and/or a storage container liner.

16. A surface covering comprising:
a multilayered composite material, wherein the multilayered composite material further includes a plurality of vertical perforated lines and a plurality of horizontal perforated lines, the vertical and horizontal perforated lines forming a grid;
and further wherein,
the multilayered composite material further comprises (1) a top facing layer of fibers resistant to stress-whitening; (2) an intermediate layer of polymeric film wherein the polymeric film is comprised of single or multiple layers of thermoplastic film; and (3) a continuous bottom layer of unsupported polyvinyl chloride foam cured by means of thermal calendaring,
wherein the top facing layer is composed of fibers that are in the range of 0.38 mm to 2.30 mm in length and the fibers are selected from the group of synthetic filaments consisting of acrylic, nylon, polyester, polypropylene, and rayon.

17. The surface covering according to claim 16, wherein the synthetic filaments have a denier weight in the range of 0.8 to 45 grams per 9000 linear meters of yarn.

18. A surface covering comprising:
a multilayered composite material, wherein the multilayered composite material further includes a plurality of vertical perforated lines and a plurality of horizontal perforated lines, the vertical and horizontal perforated lines forming a grid;
and further wherein, the multilayered composite material further comprises (1) a top facing layer of flocked synthetic fibers; (2) an intermediate layer of polymeric film wherein the polymeric film is comprised of single or multiple layers of thermoplastic film, wherein the flocked synthetic fibers are bonded to the intermediate layer; and (3) a continuous bottom layer of unsupported polyvinyl chloride foam.

19. A surface covering comprising:
a multilayered composite material, wherein the multilayered composite material further includes a plurality of vertical perforated lines and a plurality of horizontal perforated lines, the vertical and horizontal perforated lines forming a grid;
and further wherein, the multilayered composite material further comprises (1) a top facing layer of flocked synthetic fibers; (2) an intermediate layer of polymeric film wherein the polymeric film is comprised of single or multiple layers of thermoplastic film, wherein the flocked synthetic fibers are bonded to the intermediate layer; and (3) a continuous bottom layer of unsupported polyvinyl chloride foam;
wherein a bottom surface of the bottom layer of unsupported polyvinyl chloride foam is configured with a fine pattern of micro-embossed indentations, wherein the vertical and horizontal perforated lines intersect the micro-embossed indentations.

20. A surface covering comprising:
a multilayered composite material, wherein the multilayered composite material further includes a plurality of vertical perforated lines and a plurality of horizontal perforated lines, the vertical and horizontal perforated lines forming a grid;
and further wherein, the multilayered composite material further comprises (1) a top facing layer of flocked synthetic fibers; (2) an intermediate layer of polymeric film wherein the polymeric film is comprised of single or multiple layers of thermoplastic film, wherein the flocked synthetic fibers are bonded to the intermediate layer; and (3) a continuous bottom layer of unsupported polyvinyl chloride foam;
wherein the flocked synthetic fibers of the top facing layer comprise cut filaments that stand in a vertical orientation along the top facing layer.

21. The surface covering of claim 20, wherein at least one the plurality of vertical perforated lines and the plurality of horizontal perforated lines is formed at an angle other than 90 degrees relative to a bottom surface of the bottom layer of unsupported foam.

* * * * *